United States Patent [19]
Anis

[11] Patent Number: 4,795,460
[45] Date of Patent: Jan. 3, 1989

[54] FLEXIBLE THREE-PIECE POSTERIOR CHAMBER LENS

[76] Inventor: Aziz Y. Anis, 7531 N. Hampton, Lincoln, Nebr. 68506

[21] Appl. No.: 52,400

[22] Filed: May 21, 1987

[51] Int. Cl.$^4$ ............................................... A61F 2/16
[52] U.S. Cl. ........................................................ 623/6
[58] Field of Search ............................................ 623/6

[56] References Cited

U.S. PATENT DOCUMENTS

| | | | |
|---|---|---|---|
| 4,242,760 | 1/1981 | Rainin | 623/6 |
| 4,361,913 | 12/1982 | Streck | 623/6 |
| 4,581,032 | 4/1986 | Grandon | 623/6 |

FOREIGN PATENT DOCUMENTS 1134196A  1/1985  U.S.S.R. ................................... 623/6

Primary Examiner—Ronald L. Frinks

[57] ABSTRACT

A posterior chamber lens implant comprising a centrally positioned lens body having a pair of opposing loop members extending therefrom with the loop members cooperating to extend completely around the lens body. One of the loop members extends from the lens body at three o'clock and extends around the lens body in a counterclockwise manner and is connected to the lens body at approximately three o'clock. The other loop member extends from the lens body at approximately nine o'clock and extends around the lens body in a clockwise manner and has its other end secured to the lens body at approximately nine o'clock. The relationship of the loop members and the lens body permits the loop members to be compressed towards the lens body to enable the implant to be inserted in the eye.

4 Claims, 1 Drawing Sheet

FLEXIBLE THREE-PIECE POSTERIOR CHAMBER LENS

BACKGROUND OF THE INVENTION

This invention relates to a posterior chamber lens and more particularly to a three-piece posterior chamber lens having compressible loops provided thereon.

The human eye is a very complex organ comprising numerous interacting elements which gather, focus, and transmit light rays to nerve endings which eventually transmit the information to the brain for image perception. The eye includes a natural crystalline lens of avascular tissue, the transparency of which depends upon the critical regularity of its fibers and the balance of its chemical constituents. Obviously, there are enumerable factors which may interfere with lens makeup and thereby affect its transparent character. No matter what the reason, a condition of opacity in the lens, commonly called cataract, reduces the visual performance of the eye. When the visual performance is reduced to an unacceptable level, surgical cataract extraction becomes a necessity.

An eye without a lens, a condition called aphakia, is obviously defective from an optical point of view in as much as it cannot properly refract incident light rays. Aphakic correction may be accomplished in three ways:

(1) thick eye glasses worn in front of the eye;
(2) contact lenses worn on the eye, or
(3) artificial intraocular lens implant within the eye.

It is this latter procedure with which the instant invention is concerned.

The structure and procedure of installing an intraocular lens is very critical because of the elements which make up the eye are extremely sensitive and subject to irreparable damage. Numerous experimental lens designs have been abandoned through the years because they caused corneal damage and other manifestations of intraocular irritation. For example, in the late 1940's and early 1950's, H. Ridley conducted clinical experiments with an artificial intraocular lens which included a lens portion having foot-like projections extending radially away therefrom. This device was placed in the posterior chamber with the feet extending between the ciliary processes and the base of the iris. The lens proved positionally unstable and resulted in unsatisfactory amounts of irritation.

Many attempts have been made to provide a satisfactory intraocular lens. In an effort to remedy the problems associated with the prior art lens implants, applicant previously has been granted U.S. Pat. Nos. 4,143,427; 4,166,293; 4,251,887 and 4,575,374.

Although applicant's previous lens implants did represent a significant advance in the art, it is believed that the invention of the co-pending application further advanced the art in that it provided a maximum contact of the position fixation element. The instant invention represents a further advance in the art in that it includes a pair of opposing compressible loops each of which extend around the lens body for greater than 180°.

Therefore, it is a principal object of this invention to provide an improved posterior chamber lens.

A further object of the invention is to provide a posterior chamber lens wherein a pair of opposing loops extend around a centrally positioned lens body with the loops being compressible.

Yet another object of the invention is to provide a lens of the type described which includes a pair of opposing loops or fixation members which may be compressed relative to the centrally positioned lens body to enable the implant to be inserted into the capsular bag.

Still another object of the invention is to provide a posterior chamber lens which will remain in place even if pressure or force is inadvertently applied to one portion of the lens.

These and other objects will be apparent to those skilled in the art.

SUMMARY OF THE INVENTION

Figure 1:
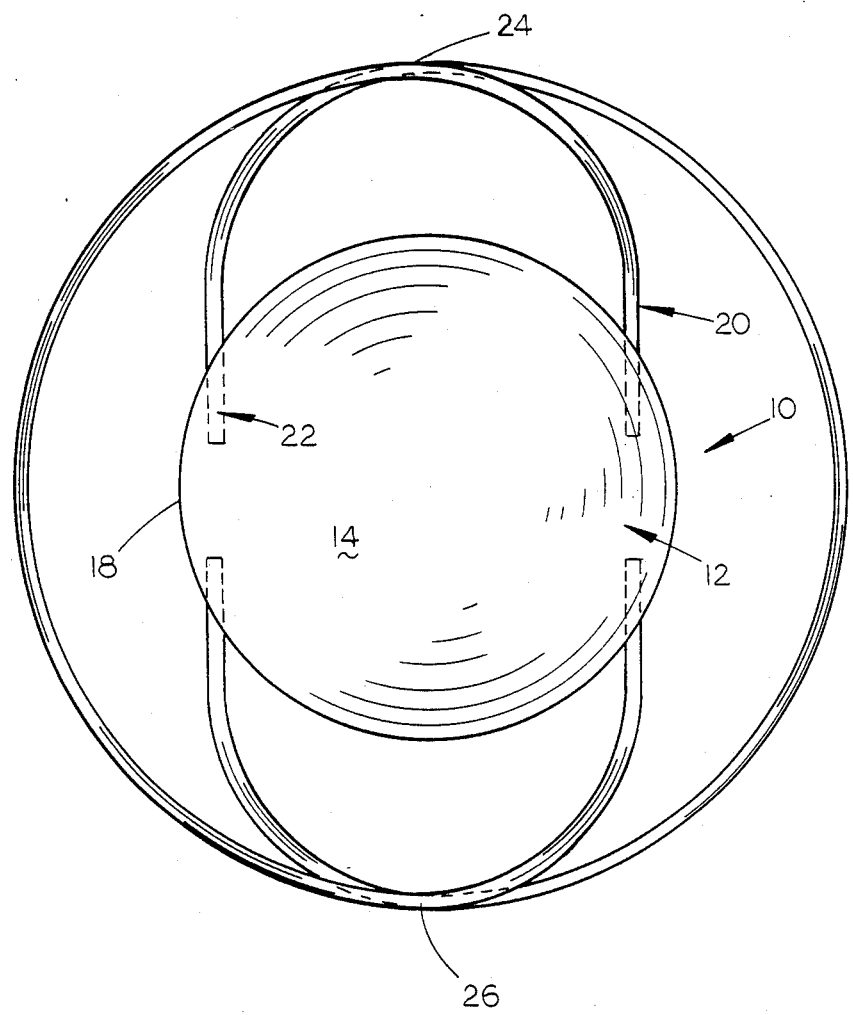
FIG. 1 is an elevational view of the invention with the broken lines indicating various positions of deflection of the position fixation member.
Figure 2:
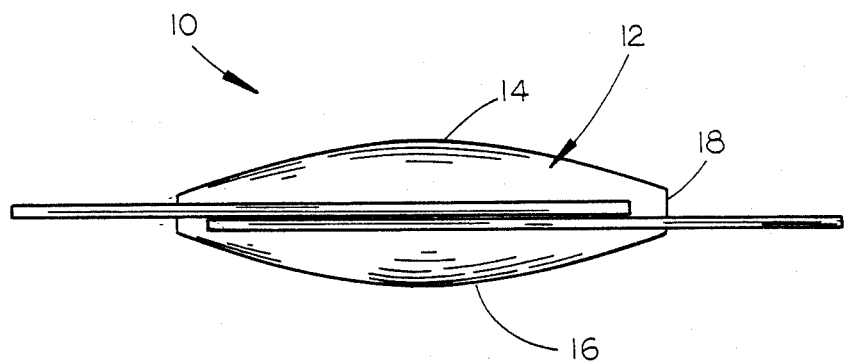
FIG. 2 is an end view of the embodiment of FIG. 1.

A posterior chamber lens implant is described which may be implanted in the eye after the natural lens of the eye has been removed. A lens implant comprises a centrally positioned lens body having a pair of opposing loop members secured thereto and extending therearound. One of the loop members extends substantially tangentially from the lens body at approximately three o'clock and extends around the lens body and in a spaced-apart relationship with respect thereto with the other end of the loop member being connected to the lens body at approximately three o'clock. The other loop member extends substantially tangentially from the lens body at approximately nine o'clock and extends around the lens body in a clockwise direction and in a spaced-apart relationship thereto with the other end of the other loop member being connected to the lens body at approximately nine o'clock. The means of connecting the loop members to the lens body permits the loop members to be compressed relative to the lens body to facilitate insertion of the implant into the eye.

DESCRIPTION OF THE PREFERRED EMBODIMENT

The lens implant of this invention is referred to generally by the reference numeral 10. Lens implant 10 includes a disc-shaped lens body 12 which may either be of the convex-plano or convex-convex configuration. For purposes of description, lens body 12 will be described as having a front face 14, back face 16 and peripheral edge 18.

A pair of fixation members or loop members 20 and 22 are secured to the lens body 12 in the opposing relationship as illustrated in the drawings. One end of the fixation member 20 is secured to the lens body 12 and extends substantially tangentially therefrom at approximately the three o'clock position. Loop member 20 extends around the lens body in a counterclockwise manner as illustrated in FIG. 1 and in a spaced-apart relationship with respect to the lens body 12. The other end of the loop member 22 is secured to the lens body 12 at approximately the three o'clock position as best seen in FIG. 1.

Loop member 22 has one end thereof secured to the lens body 12 at approximately the nine o'clock position and extends substantially tangentially therefrom as illustrated in FIG. 1. Loop member 22 extends around the lens body 12 in a spaced-apart relationship and in a clockwise manner. The other end of loop member 22 is secured to the lens body 12 at substantially the nine o'clock position as seen in FIG. 1. Preferably, loop members 20 and 22 dwell in slightly different planes so that they may intersect without substantial contact at 24 and 26 although the loop members 20 and 22 may be positioned in the same plane if desired which will require that the loop members "cross-over" at 24 and 26. Further, the loop members 20 and 22 may be offset with respect to the lens body.

The primary feature of the instant invention is that the loop members cooperate with each other so that the loop members extend around the lens body for 360° to enable the maximum contact of the fixation members within the eye. The lens may be inserted in any position within the eye since there is not a top or bottom portion of the lens implant. The loop members 20 and 22 together define a generally continuous circular periphery which is adapted to engage the periphery of the capsular sac over substantially 360 degrees. The 360° engagement of the fixation members with the eye positively ensures that the lens implant will remain in position and will not become inadvertently dislodged.

Preferably, lens body 14 has a diameter of 6 millimeters but the same can be between 4.0 and 8.0 millimeters. Preferably, the diameter of fixation members 20 and 22, when cooperating together, is between 10.5 millimeters but the same can vary between 8.0 millimeters and 13.0 millimeters. Preferably, the diameter of each of the fixation or loop members 20 and 22 is 0.15 millimeters.

The construction of the lens implant 10 is such that the fixation members 20 and 22 engage the capsular bag for 360°. The loop members 20 and 22 aid in centrally positioning the lens body 14 with respect to the eye. The construction of the lens implant 10 is such that the fixation members 20 and 22 may be compressed towards the lens body 14, as illustrated by the broken lines in FIG. 1, to enable the implant 10 to be inserted into the capsular bag.

Thus it can be seen that the invention accomplishes at least all of its stated objectives.

I claim:

1. A lens implant, comprising:
  a lens body; and
  a pair of elongated flexible loop members secured to said lens body in an opposing relationship with respect to each other, whereby said flexible loop members may be compressed toward said lens body to permit insertion into the capsular sac;
  said loop members cooperating together to extend around said lens body for at least 360 degrees;
  said lens body being disc-shaped;
  one of said loop members having one end secured to said lens body at approximately the three o'clock position extending around the lens body in a spaced-apart relationship with respect thereto and having its other end secured to said lens body at approximately the three o'clock position;
  the other of said loop members having one end secured to said lens body at approximately the nine o'clock position extending around the lens body in a spaced-apart relationship with respect thereto and having its other end secured to said lens body at approximately the nine o'clock position, wherein said lens body is held centrally by said flexible loop members, said loop members together defining a generally continuous circular periphery which is adapted to engage the periphery of the capsular sac over substantially 360 degrees.

2. The lens implant of claim 1 wherein said loop members dwell in substantially the same plane.

3. A lens implant according to claim 1 in which the loop members extend substantially tangentially from the lens body.

4. A lens implant according to claim 1 wherein the loop members are offset sufficiently to permit their intersection.

* * * * *